(12) United States Patent
Mazzarolo et al.

(10) Patent No.: US 8,832,871 B2
(45) Date of Patent: Sep. 16, 2014

(54) NECK PROTECTIVE COLLAR WITH SAFETY BREAKABLE STRUCTURE

(75) Inventors: Giovanni Mazzarolo, Coste di Maser (IT); Colin Ballantyne, Caselle d'Asolo (IT)

(73) Assignee: Alpinestars Research SRL, Coste di Maser (Treviso) (IT)

(*) Notice: Subject to any disclaimer, the term of this patent is extended or adjusted under 35 U.S.C. 154(b) by 427 days.

(21) Appl. No.: 12/743,448

(22) PCT Filed: Mar. 6, 2009

(86) PCT No.: PCT/IB2009/050938
§ 371 (c)(1),
(2), (4) Date: May 18, 2010

(87) PCT Pub. No.: WO2009/109944
PCT Pub. Date: Sep. 11, 2009

(65) Prior Publication Data
US 2010/0263112 A1    Oct. 21, 2010

(30) Foreign Application Priority Data

Mar. 6, 2008 (IT) ................. TV2008A0039

(51) Int. Cl.
| | | |
|---|---|---|
| *A41D 13/00* | (2006.01) | |
| *A61F 5/055* | (2006.01) | |
| *A42B 3/04* | (2006.01) | |
| *A41D 13/05* | (2006.01) | |

(52) U.S. Cl.
CPC ............... *A61F 5/055* (2013.01); *A42B 3/0473* (2013.01); *A41D 13/0512* (2013.01)
USPC ............................................................. 2/468

(58) Field of Classification Search
USPC .......................... 2/422, 455, 468; 602/17–19
See application file for complete search history.

(56) References Cited

U.S. PATENT DOCUMENTS

| 2,820,455 A | 12/1953 | Hall |
| 3,076,206 A | 2/1963 | Kinney |

(Continued)

FOREIGN PATENT DOCUMENTS

| DE | 27 17 712 A1 | 10/1978 |
| DE | 31 36 466 A1 | 4/1983 |

(Continued)

OTHER PUBLICATIONS

English-language Abstract FR2700746 (Schegerin).

(Continued)

*Primary Examiner* — Katherine Moran
(74) *Attorney, Agent, or Firm* — Fredrikson & Byron, P.A.

(57) ABSTRACT

A collar for protecting the neck of a user, useful in particular for motorcycle riders, is envisaged, said collar comprising two half-collars which are pivotably hinged together at one end so as to be rotatable in a substantially horizontal plane and which can be connected together by means of a fastening and release lever, a safety structure which at the rear extends downwards from the bottom edge of the collar so as to be centered with respect to the spinal column of the user, and a protective shield which extends downwards at the front. The safety structure has a breakable structure made of the material with an impact strength lower than the material forming the collar so as to break in a programmed manner in the event of impacts following falls.

20 Claims, 5 Drawing Sheets

(56) References Cited

U.S. PATENT DOCUMENTS

Figure 1:
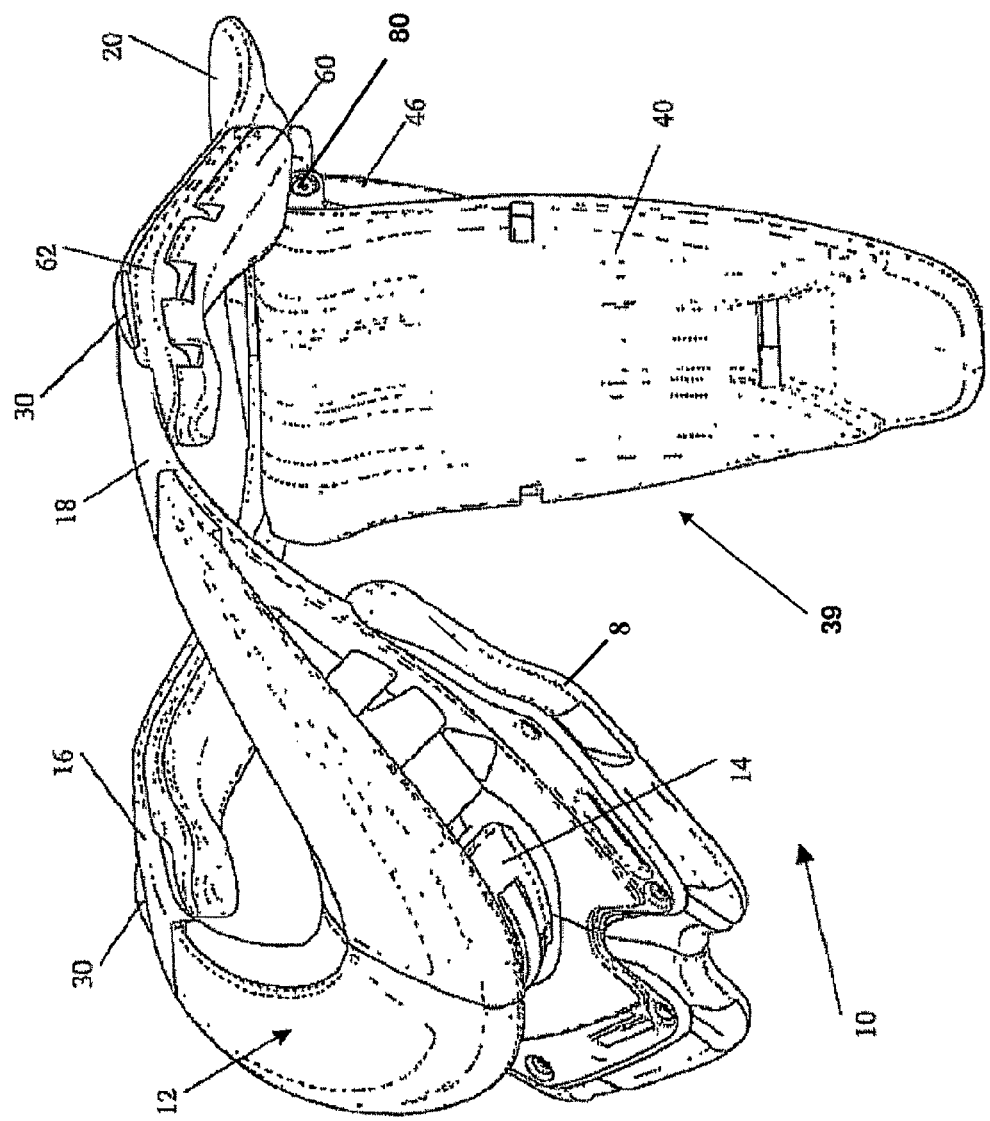

| | | | |
|---|---|---|---|
| 3,202,307 | A | 8/1965 | Rainer |
| 3,477,425 | A | 11/1969 | Grassi |
| 3,495,272 | A | 2/1970 | Tempelhof |
| 3,765,412 | A | 10/1973 | Ommaya et al. |
| 3,849,801 | A | 11/1974 | Holt |
| 3,855,631 | A | 12/1974 | Ettinger |
| 3,858,241 | A * | 1/1975 | Durand et al. .............. 2/2.5 |
| 3,878,561 | A | 4/1975 | Winiecki |
| 4,274,161 | A | 6/1981 | Littler |
| 4,319,362 | A | 3/1982 | Ettinger |
| 4,422,454 | A | 12/1983 | English |
| 4,441,211 | A | 4/1984 | Donzis |
| 4,449,251 | A | 5/1984 | Gauthier |
| 4,501,023 | A | 2/1985 | Bilberry |
| 4,502,471 | A | 3/1985 | Owens |
| 4,554,681 | A | 11/1985 | Kirkland |
| 4,675,912 | A | 6/1987 | Kirkland |
| 4,821,339 | A | 4/1989 | Fair |
| 4,854,306 | A | 8/1989 | Pujals |
| 4,989,265 | A | 2/1991 | Nipper |
| 4,996,720 | A | 3/1991 | Fair |
| 5,003,968 | A | 4/1991 | Mars |
| 5,039,035 | A | 8/1991 | Fitzpatrick |
| 5,133,084 | A | 7/1992 | Martin |
| 5,230,698 | A | 7/1993 | Garth |
| 5,411,471 | A | 5/1995 | Terrazas |
| 5,437,613 | A | 8/1995 | Reggio et al. |
| 5,517,699 | A | 5/1996 | Abraham, II |
| 5,531,669 | A | 7/1996 | Varnau |
| 5,546,609 | A | 8/1996 | Rush, III |
| 5,590,826 | A | 1/1997 | Endo |
| 6,058,517 | A | 5/2000 | Hartunian |
| 6,067,665 | A | 5/2000 | DePalma et al. |
| 6,494,854 | B1 | 12/2002 | Visness et al. |
| 6,729,643 | B1 | 5/2004 | Bassick |
| 7,017,194 | B2 | 3/2006 | Schroth |
| 7,041,073 | B1 | 5/2006 | Patron |
| 7,329,230 | B2 | 2/2008 | Mazzarolo |
| 7,371,221 | B1 | 5/2008 | Baker |
| 2004/0167448 | A1 | 8/2004 | Hefez |
| 2007/0010771 | A1 * | 1/2007 | Leatt .............. 602/18 |
| 2007/0106194 | A1 | 5/2007 | Pickering |
| 2007/0281125 | A1 * | 12/2007 | Moore et al. .............. 428/71 |
| 2010/0056968 | A1 * | 3/2010 | Mazzarolo .............. 602/18 |
| 2010/0121238 | A1 | 5/2010 | Mazzarolo |
| 2010/0235973 | A1 | 9/2010 | Mazzarolo |
| 2010/0251468 | A1 | 10/2010 | Mazzarolo |
| 2011/0004980 | A1 | 1/2011 | Leatt et al. |

FOREIGN PATENT DOCUMENTS

| | | |
|---|---|---|
| DE | 295 21 373 U1 | 4/1997 |
| DE | 195 45 299 A1 | 6/1997 |
| DE | 200 06 084 U1 | 8/2001 |
| EP | 0023115 A | 1/1981 |
| EP | 0043990 A1 | 1/1982 |
| FR | 2534115 A | 4/1984 |
| FR | 2700746 | 7/1994 |
| FR | 2719747 | 11/1995 |
| GB | 2 126 485 A | 3/1984 |
| JP | 5747235 | 3/1982 |
| JP | 200014686 | 1/2000 |
| SL | 9600306 A | 4/1998 |
| WO | 9809545 A1 | 3/1998 |
| WO | 9938401 A1 | 8/1999 |
| WO | 0125088 | 4/2001 |
| WO | 02089620 A1 | 11/2002 |
| WO | 03077793 A2 | 9/2003 |
| WO | 03092561 | 11/2003 |
| WO | 2005051251 A | 6/2005 |
| WO | 2005107658 A | 11/2005 |
| WO | 2008050307 | 5/2008 |

OTHER PUBLICATIONS

English-language Abstract FR2719747 (Streiff Motorsport).
English-language Abstract FR2534115 (Nolan SPA).
"PCT International Search Report dated May 13, 2009 for PCT/IB2009/050938, from which the instant application is based," 3 pgs.
"PCT Demand with attachments dated Dec. 28, 2009 for PCT/IB2009/050938, from which the instant application is based," 7 pgs.
"PCT Written Opinion dated May 13, 2009 for PCT/IB2009/050938, from which the instant application is based," 4 pgs.
"PCT International Search Report dated May 12, 2009 for PCT/IB2009/050936," 2 pgs.
"PCT Demand with attachments dated Dec. 28, 2009 for PCT/IB2009/050936," 12 pgs.
"PCT International Search Report dated May 15, 2009 for PCT/IB2009/050934," 2 pgs.
"PCT Written Opinion dated May 15, 2009 for PCT/IB2009/050934," 5 pgs.
"PCT International Preliminary Report on Patentability dated May 27, 2010 for PCT/IB2009/050938, from which the instant application is based," 4 pgs.
"PCT International Preliminary Report on Patentability dated May 26, 2010 for PCT/IB2009/050936," 6 pgs.

* cited by examiner

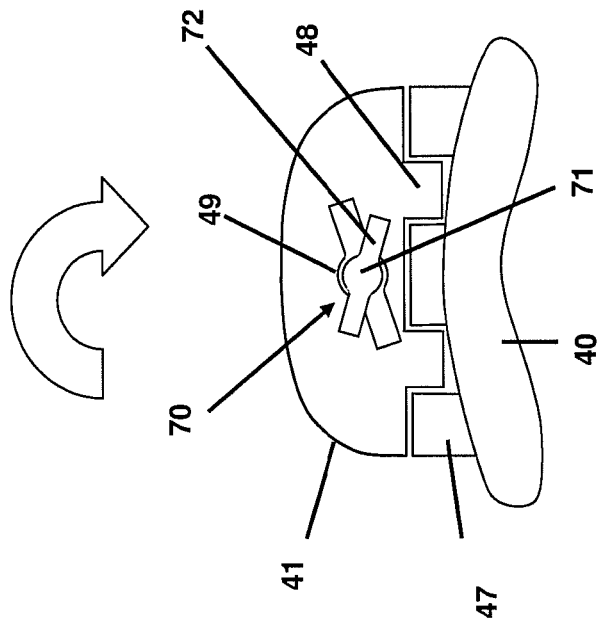
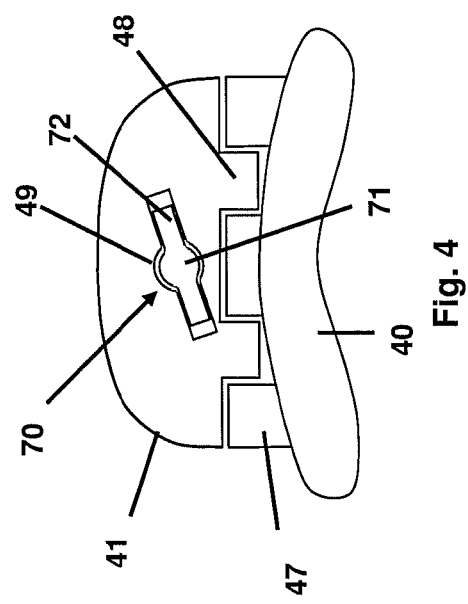

NECK PROTECTIVE COLLAR WITH SAFETY BREAKABLE STRUCTURE

RELATED APPLICATIONS

This application is a 35 U.S.C. 371 national stage filing from International Application No. PCT/IB2009/050938 filed Mar. 6, 2009 and claims priority to Italian Application No. TV2008A000039 filed Mar. 6, 2008, the teachings of which are incorporated herein by reference.

This invention relates to a protective collar, useful during sporting activities, especially when riding motorcycles.

Various protective collars intended for persons who practise sporting activities are known and are commercially available. The obvious objective is to protect a part of the human body, such as the neck, which is extremely delicate and prone to fractures and knocks. In the event of a fall, for example from a motorcycle travelling at speed, it has been known that the neck often suffers damage, despite the fact that the rider is wearing a conventional protective helmet.

An example of a collar for motocross is described in the international patent application No. WO 2005/051251 in the name of Leatt.

This collar consists of two sections which are releasably connected together by means of a side hinge. The collar has surfaces which are directed upwards and limit the inclination of the head in all directions when the helmet is worn.

The collar rests on the user's shoulders by means of a padding permanently fixed to its bottom edge and has a plate extending at the rear downwards from its rear edge, with the function of transferring to the sides of the spinal column loads acting on the user's back, so that they are unable to act on the spine itself.

This type of collar, as well as other collars which are known from the prior art, however, have various problems and drawbacks.

In the event of an accident or fall, both the rigid side hinge and the rear plate may constitute a danger for the rider, especially if they are deformed or break.

The object of the invention is to provide a collar which solves substantially the abovementioned problems and drawbacks and is easy to use, in addition to protecting the user in an effective manner.

In particular, the object of the present invention is to provide a collar which, in case of accident or impact, is able to reduce the chance that a catastrophic neck injury happens.

Figure 2:
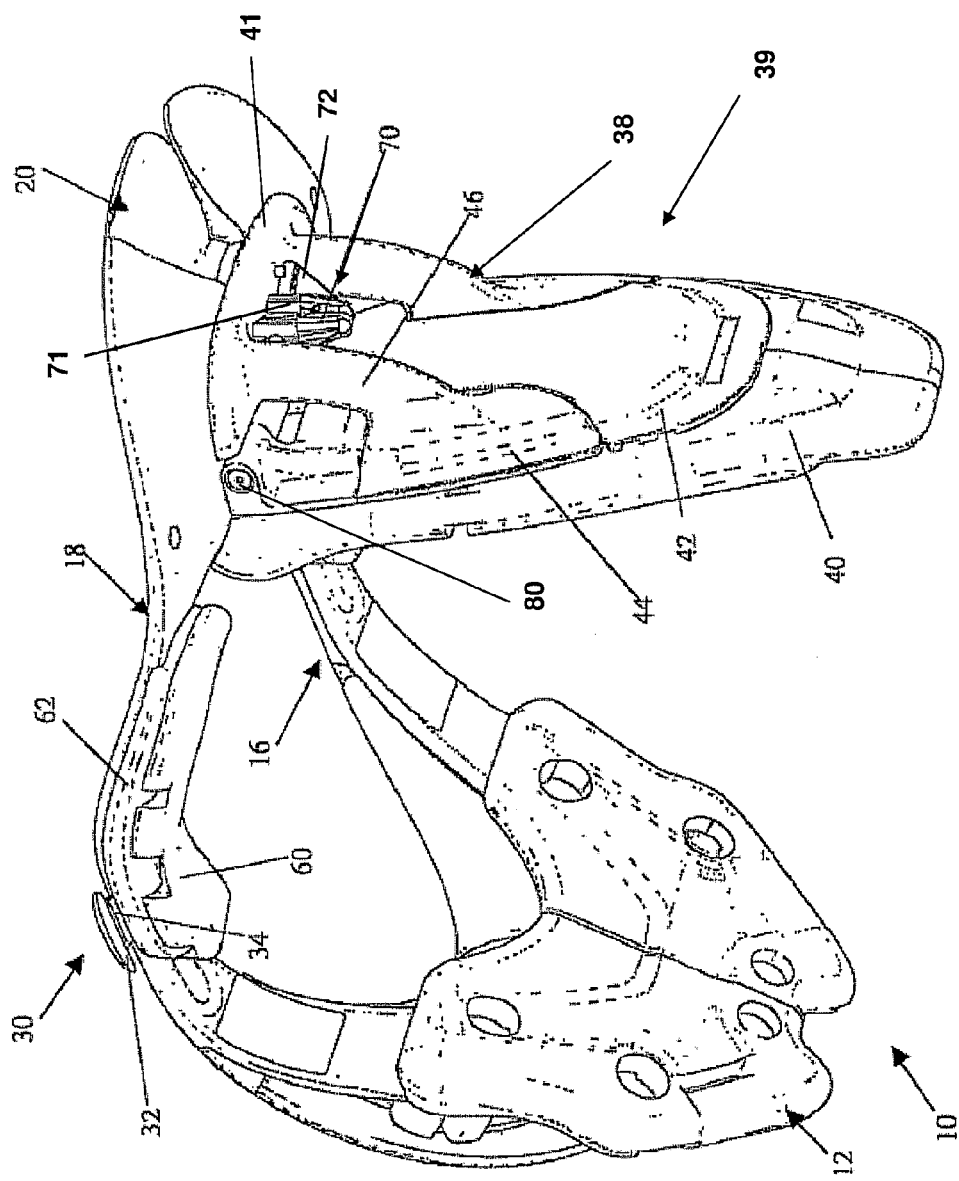

With reference to FIGS. 1 and 2, these objects are achieved with a collar 10 for protecting the neck of a user, useful in particular for motorcycle riders, of the type comprising two half-collars 16, 18 which are pivotally hinged together at one end so as to be rotatable in a substantially horizontal plane and which can be connected together by means of a fastening and release lever 14 located at a front of the collar, a plate 42 which at the rear extends downwards from the bottom edge of the collar 10 so as to be centered with respect to the spinal column of the user, and a protective shield 8 which is connected to and extends downwards from a front of the collar 10, characterized in that said plate 42 extending at the rear and resting on the user's back has a structure 38 designed to break or collapse in a programmed manner in a direction parallel to the spinal column of the user following an impact. As further shown in FIG. 1, the shield 8 is connected underneath the front of the collar 10.

Figure 3:
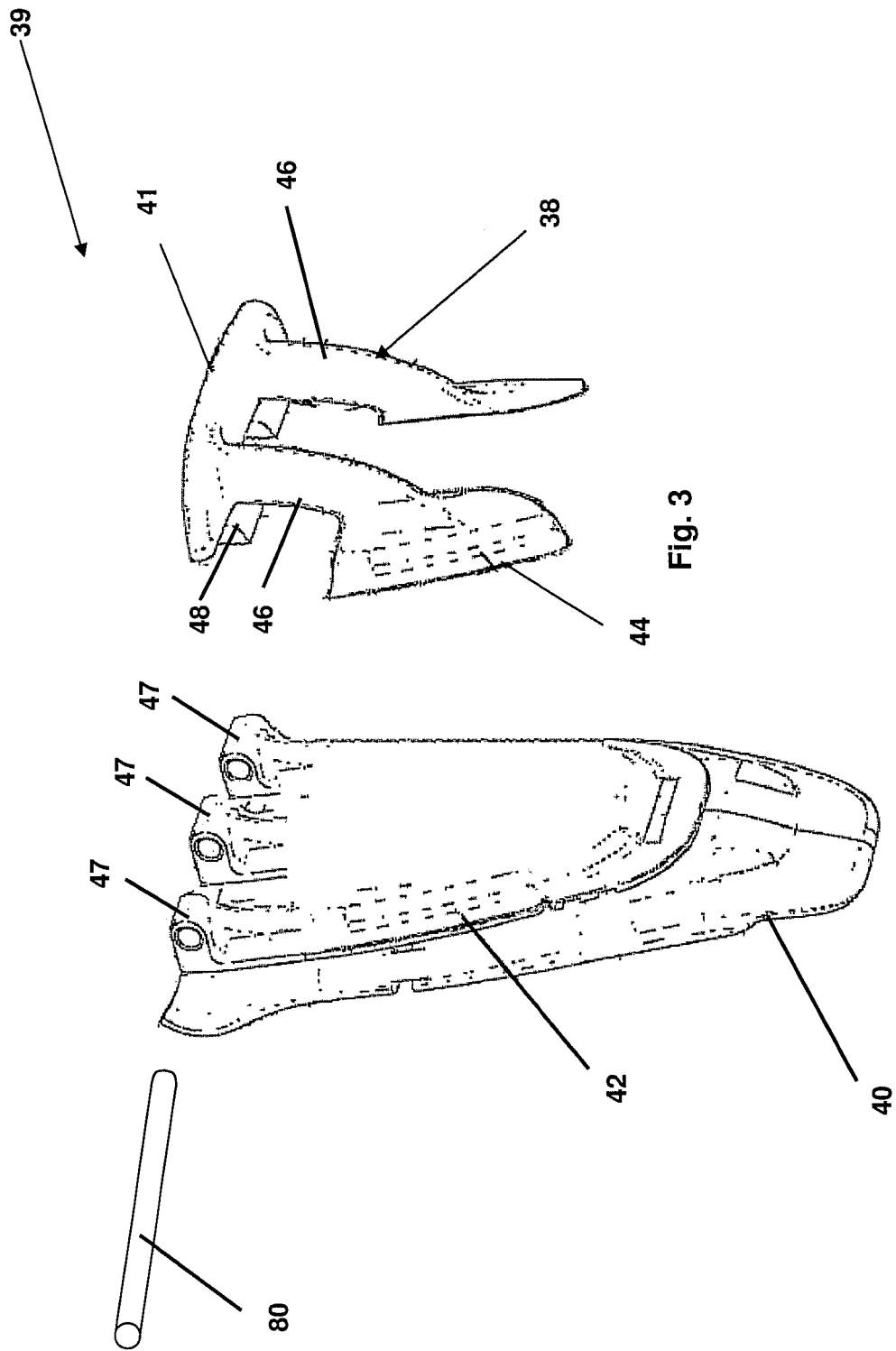
Figure 6:
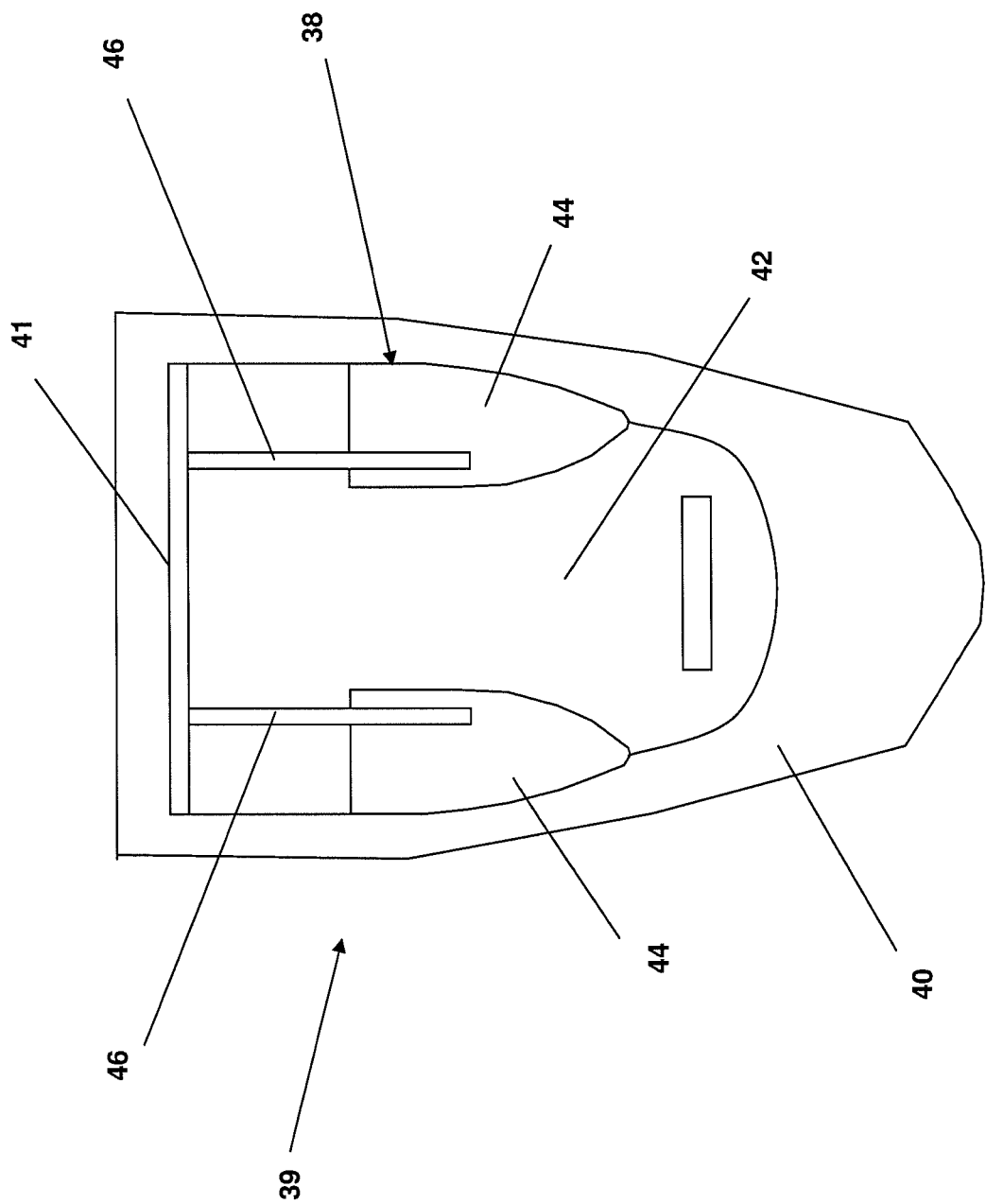

The advantages of the invention will be explained more fully by the following description, intended purely by way of a non-limiting example, of a preferred embodiment of a collar, shown in the accompanying drawings in which:

FIG. 1 shows a three-dimensional front view of the collar;
FIG. 2 shows a three-dimensional rear view of the collar according to FIG. 1;
FIG. 3 shows an exploded view of the principal parts of the rear structure of the collar;
FIG. 4 shows a schematic top view of the rear structure of the collar when the structure is not fixed to the collar;
FIG. 5 shows a schematic top view of the rear structure of the collar when the structure is fixed to the collar;
FIG. 6 shows a schematic rear view of the rear structure of the collar.

With reference first of all to FIGS. 1 and 2, there is shown a collar 10 which has a symmetrical structure and consists of a front part 12, which rests on the chest, closed by a fastening lever 14, two side segments 16, 18 which are nearly flat, and a rear part 20.

The segments 16, 18 are hinged together by means of a rear pin 70 and may be opened wide apart so that the neck can be inserted inside the collar 10. The fastening lever 14 has the function of fastening together the segments 16, 18 in the closed position such that, during use, the collar 10 has an annular structure which surrounds the neck completely.

The segments 16, 18 have a cross-section in the form of a rounded rectangle and each of them has, mounted on the edge towards the outside of the collar 10, a tongue 30 which is formed by a central body 34 which terminates in a right-angled extension 32 widened in the form of a mushroom head.

Two pads 60, 62 are mounted underneath each of the segments 16, 18, being arranged on top of each other.

Considering FIGS. 1, 3, 4, 5 and 6, as already mentioned, the rear part 20 extends downwards with a support safety structure 39. The latter consists of a vertical plate 42 which has, fixed thereto, a breakable part 38.

The breakable part 38 comprises two ribs 46 which are connected together at the top end forming a platform 41 which in turn is positioned so as to make contact against the bottom surface of the rear part 20. The two ribs 46 are fixed to the plate 42 through bases 44 having a widened form (FIG. 6).

The breakable part 38 is made of a plastic material which has a lower impact strength than both the material forming the plate 42 and the segments 16 and 18, so that, when the breakable part 38 is subjected to high and sudden axial and lateral loads, it fails, which as a result absorbs impact energy.

To the rear part of the plate 42 a pad 40 is provided which abuts against the user's back through a part or layer of foamed plastic, e.g. polypropylene with a density of between 65 and 75 g/l. The pad 40 is able to bend or deform when it's subjected to an impact or a load.

According to a preferred embodiment, the support safety structure 39 can be fixed, in a non-permanent manner, to the rear part 20 of the collar 10 by the fixing pin 70.

The pin 70 is fixed to the two half-collars 16, 18 and is formed by a substantially cylindrical central body 71 having two side extension 72 shaped as right triangle.

This pin 70 engages the platform 41 by entering a slot 49 provided in the platform 41. This slot 49 has a substantially rectangular shape, with a central circular opening suitable for housing the central body 71 of the pin 70.

The structure 39 is assembled with the rear part 20 of the neck collar 10 when the collar 10 is not worn.

In fact, with the collar upside down, the structure 39 is positioned at the top of the pin 70 (FIG. 4), it is then pushed down so such that the underside of the tail of the rear part 20, and the top surface of the platform 41 make contact. Finally it is turned in a clockwise direction such that the slot 49 is not lined up with the side extension 72 of the pin 70 (FIG. 5)

In this way the structure 39 reaches its position and is locked to the rear part 20 of the collar 10.

Moreover, on the edge of the platform 41 abutting against the plate 42, two cylindrical bushes 48 can be arranged. A pin 80 is inserted into these bushes 48 and is also coupled to three bushes 47 provided at the top zone of the plate 42, to allow the breakable structure 38 to be joined to the plate 42 by means of a hinge.

This removable fixing allows the breakable structure 38 to be replaced if it is weakened or broken in an accident.

As a result, after the replacement of the breakable structure 38, if no further damages are discovered, the collar 10 will be reusable.

The replacement of said breakable structure 38 is easy for the user.

Firstly, the structure 39 is removed from the collar 10 by a counterclockwise rotation around the pin 70 and then the pin 80 is extracted from the bushes (47, 48) to separate the plate 42 from the breakable structure 38.

After the replacement of the weakened breakable structure 38 with a new breakable structure 38, the pin 80 must be reinserted into the bushes 47, 48 for fixing again the breakable structure 38 to the plate 42.

The structure 39 subsequently can be fixed to the collar 10, by the pin 70.

From the above description it is clear that the collar according to the present invention has characteristics such as to solve advantageously the problems and drawbacks of the devices according to the prior art.

The present invention has been described with reference to a preferred embodiment, but mechanically equivalent solutions are foreseeable falling within the scope of the appended claims. For instance mechanical arrangements for fixing the structure 39 to the rear part of the collar 20 permitting the structure to be removed from the rear part and to be pivotally connected to allow for the rotation of the structure around a horizontal axis and thus adjust the structure to the back of the user.

The invention claimed is:

1. Collar for protecting a neck of a user, useful for motorcycle riders, of the type comprising:
   two half-collars which are pivotally hinged together at one end so as to be rotatable in a substantially horizontal plane and which can be connected together by means of a fastening and release lever;
   a safety structure which at a rear of the collar extends downwards from a bottom edge of the collar so as to be centered with respect to a spinal column of the user; and
   a protective shield which is connected to and extends downwards from a front of the collar;
   wherein said safety structure comprises a plate and a breakable structure, said breakable structure being made of a material with a lower impact strength than material forming said plate and said half-collars, wherein said breakable structure has two projecting ribs with respect to a plane of said plate.

2. The collar of claim 1 wherein the breakable structure is a body that is separate from the collar.

3. The collar according to claim 2, wherein said safety structure is fixed, in a non-permanent manner, to a rear part of the collar by a fixing pin.

4. The collar according to claim 2, wherein said breakable structure is fixed, in a non-permanent manner, to said plate.

5. The collar according to claim 2, wherein the body is configured to break from impact without breakage occurring to the two half collars.

6. The collar according to claim 2, wherein the body is a replaceable member of the collar, wherein the collar is reusable if the body is broken from impact and subsequently replaced.

7. The collar according to claim 2, wherein the body is selectively separable from the collar.

8. The collar of claim 2, wherein the body is fixed to the collar and configured to be released from the collar via rotation of the body and thereby corresponding rotation of a slot defined in the body with respect to a pin that protrudes from the collar and has an end shaped to pass through the slot when aligned with the slot.

9. The collar according to claim 1, wherein said ribs are connected at a top end forming a platform, a top surface of said platform making contact against an underside of a tail of a rear part of the collar.

10. The collar according to claim 9, wherein the connection between the breakable structure and the plate is made by a pin which is housed in bushes provided at the plate and the top end of the platform.

11. The collar according to claim 1, wherein the two ribs are fixed to the plate through bases having widened form.

12. The collar according to claim 1, wherein said safety structure further comprises a pad abutting against a back of the user, said pad being suitable to bend or deform when subjected to a load.

13. The collar according to claim 12, wherein said pad is made of foamed plastic.

14. The collar according to claim 13, wherein said foamed plastic is foamed polypropylene with a density of between 65 and 75 g/l.

15. The collar according to claim 1, wherein said safety structure is fixed, in a non-permanent manner, to a rear part of the collar by a fixing pin.

16. The collar according to claim 1, wherein said breakable structure is fixed, in a non-permanent manner, to said plate.

17. The collar of claim 1, wherein the shield is connected underneath the front of the collar.

18. The collar of claim 1, wherein the collar further comprises a fastening and release lever located at a front of the collar, the lever used for connecting together the half collars at said front of the collar.

19. Collar for protecting a neck of a user, useful for motorcycle riders, of the type comprising:
   two half-collars which are pivotally hinged together at one end so as to be rotatable in a substantially horizontal plane;
   a fastening and release lever located at a front of the collar and used for connecting together the two half collars at said front of the collar;
   a safety structure which at a rear of the collar extends downwards from a bottom edge of the collar so as to be centered with respect to a spinal column of the user; and
   a protective shield which is connected to and extends downwards from the front of the collar;
   wherein said safety structure comprises a plate and a breakable structure, said breakable structure being made of a material with a lower impact strength than material forming said plate and said half-collars.

20. Collar for protecting a neck of a user, useful for motorcycle riders, of the type comprising:
   two half-collars which are pivotally hinged together at one end so as to be rotatable in a substantially horizontal plane and which can be connected together by means of a fastening and release lever;

a safety structure which at a rear of the collar extends downwards from a bottom edge of the collar so as to be centered with respect to a spinal column of the user; and a protective shield which is connected to and extends downwards from a front of the collar;

wherein said safety structure comprises a plate and a breakable structure, said breakable structure being made of a material with a lower impact strength than material forming said plate and said half-collars, and wherein the breakable structure is a body that is separate from the collar, the body being fixed to the collar and configured to be released from the collar via rotation of the body and thereby corresponding rotation of a slot defined in the body with respect to a pin that protrudes from the collar and has an end shaped to pass through the slot when aligned with the slot.

* * * * *